US011977090B2

(12) United States Patent
Degen et al.

(10) Patent No.: US 11,977,090 B2
(45) Date of Patent: May 7, 2024

(54) WALK-AWAY TIME VISUALIZATION METHODS AND SYSTEMS

(71) Applicant: Siemens Healthcare Diagnostics Inc., Tarrytown, NY (US)

(72) Inventors: Heinrich Helmut Degen, Plainsboro, NJ (US); Sara Kendrick, Dallas, TX (US); Scott Salmon, Tenafly, NJ (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 114 days.

(21) Appl. No.: 17/632,788

(22) PCT Filed: Aug. 3, 2020

(86) PCT No.: PCT/US2020/044723
§ 371 (c)(1),
(2) Date: Feb. 3, 2022

(87) PCT Pub. No.: WO2021/026062
PCT Pub. Date: Feb. 11, 2021

(65) Prior Publication Data
US 2022/0291247 A1 Sep. 15, 2022

Related U.S. Application Data

(60) Provisional application No. 62/882,724, filed on Aug. 5, 2019.

(51) Int. Cl.
*G01N 35/00* (2006.01)
*G16H 10/40* (2018.01)

(52) U.S. Cl.
CPC ... *G01N 35/0092* (2013.01); *G01N 35/00594* (2013.01); *G16H 10/40* (2018.01); *G01N 2035/0094* (2013.01)

(58) Field of Classification Search
CPC ......... G01N 35/0092; G01N 35/00594; G01N 2035/0094; G16H 10/40
See application file for complete search history.

(56) References Cited

U.S. PATENT DOCUMENTS 5,437,838 A 8/1995 Demoranville et al.
5,940,829 A * 8/1999 Tsuiki ................ G06Q 10/0633
(Continued)

FOREIGN PATENT DOCUMENTS

JP 2009-47683 A 3/2009
JP 2011-112489 A 6/2011
(Continued)

OTHER PUBLICATIONS

PCT International Search Report and Written Opinion dated Oct. 5, 2020 (13 Pages).
(Continued)

*Primary Examiner* — Shogo Sasaki (57) ABSTRACT

A status visualization method of a diagnostic laboratory system. The status visualization method includes receiving, at a system controller, computer-readable data comprising analyzers included within the diagnostic laboratory system, and test demand for types of tests and number of the tests to be performed on samples by the analyzers, wherein the analyzers each include consumable items and maintenance items. The method further includes determining, via a walk-away time estimation module executing on the system controller, an estimated walk-away time for the analyzers based upon the test demand and status of the consumable items and maintenance items. Diagnostic laboratory systems with walk-away time estimation are disclosed, as are other aspects.

19 Claims, 9 Drawing Sheets

(56) References Cited

U.S. PATENT DOCUMENTS

| | | | |
|---|---|---|---|
| 7,904,097 B2* | 3/2011 | Misikangas | G01S 5/02524 |
| | | | 455/403 |
| 9,079,178 B2 | 7/2015 | Sheldon | |
| 9,207,251 B2 | 12/2015 | Bernet et al. | |
| 9,953,141 B2* | 4/2018 | Scott | G16H 10/40 |
| 2003/0021728 A1 | 1/2003 | Sharpe, Jr. et al. | |
| 2004/0090333 A1* | 5/2004 | Wildman | G08B 21/245 |
| | | | 340/573.1 |
| 2008/0186231 A1* | 8/2008 | Aljadeff | G01S 5/06 |
| | | | 342/387 |
| 2008/0312893 A1 | 12/2008 | Denton | |
| 2010/0123560 A1* | 5/2010 | Nix | H04Q 9/00 |
| | | | 340/10.4 |
| 2013/0043361 A1 | 2/2013 | Bernet et al. | |
| 2015/0011970 A1 | 1/2015 | Kamen et al. | |
| 2015/0093834 A1 | 4/2015 | Knecht et al. | |
| 2018/0080949 A1 | 3/2018 | Jost et al. | |
| 2018/0327708 A1 | 11/2018 | Cannon et al. | |

FOREIGN PATENT DOCUMENTS

| | | |
|---|---|---|
| JP | 2014-526687 A | 10/2014 |
| WO | 2019/102282 A1 | 5/2019 |

OTHER PUBLICATIONS

Ratnam, Sam et al: "Workflow and Maintenance Characteristics of Five Automated Laboratory Instruments for the Diagnosis of Sexually Transmitted Infections", Journal of Clinical Microbiology, Jul. 2014, vol. 52, No. 7; pp. 2299-2304.

* cited by examiner

WAT Items Input Screen — 346

Analyzer 1

| Consumable Item | # tests | Tot. WAT Add |
|---|---|---|
| Diluent | 150 tests | + 450 minutes |
| Bulk Reagent | 100 tests | + 300 minutes |
| Test-Specific Reagent A | 20 tests | + 300 minutes |
| Wash Liquid | 100 tests | + 300 minutes |
| Pipette Tips | 150 tests | + 450 minutes |
| ⋮ | | |
| Reaction Vessels | 150 tests | + 450 minutes |

| Maintenance Item | | |
|---|---|---|
| Empty Solid Waste = | 8 lb. | + 250 minutes |
| Empty Liquid Waste = | 8 lb. | + 75 minutes |

WALK-AWAY TIME VISUALIZATION METHODS AND SYSTEMS

CROSS REFERENCE TO RELATED APPLICATION

This application claims priority to U.S. Provisional Patent Application No. 62/882,724, entitled "PROACTIVE AND PREDICTIVE WALKAWAY TIME" filed Aug. 5, 2019, the disclosure of which is hereby incorporated by reference in its entirety for all purposes.

FIELD

This disclosure relates to methods and systems that provide operational information of a diagnostic laboratory having one or more analyzers.

BACKGROUND

Diagnostic laboratories include medical devices for conducting in-vitro tests ("analyzers") that process test orders received from a laboratory information system (LIS) in a semi-automated manner. In some systems, a lab technician can load biological samples on the various analyzers of the laboratory, define the tests to be conducted, and load necessary test materials (e.g. test specific reagents, bulk reagents, diluent, wash liquid, reaction vessels and pipette tips) and run the tests on the analyzers. After starting the tests on each analyzer, the lab technician can walk away from those analyzers for a time and focus on other tasks in the laboratory, while the analyzers process the samples and produce the test results automatically. The amount of time that a lab technician can walk away from any particular analyzer is referred to as "walk-away time" (WAT) for that analyzer. However, it is difficult for the lab technician (s) to understand WAT for any particular analyzer, and especially within a diagnostic laboratory that includes a large number of analyzers due to changing test demand and the sheer number of items that need to be addressed.

Accordingly, there is an unmet need to improve operation and understanding of WAT for analyzers and for diagnostic laboratories including a large number of analyzers.

SUMMARY

According to a first embodiment, a status visualization method of a diagnostic laboratory is provided. The method includes receiving, at a system controller, computer-readable data comprising an inventory of analyzers included within the diagnostic laboratory, and test demand for types of tests and number of the tests to be performed on samples by the analyzers, wherein the analyzers each include consumable items and maintenance items; and determining, via a walk-away time estimation module executing on the system controller, an estimated walk-away time for the analyzers based upon the test demand and status of the consumable items and maintenance items.

According to another embodiment, a method of a diagnostic laboratory is provided. The method includes receiving, at a system controller, computer-readable data about a plurality of analyzers included within the diagnostic laboratory, and test demand for types of tests and number of the tests to be performed on samples by the plurality of analyzers, wherein the plurality of analyzers each include consumable items and maintenance items; determining, via a walk-away time prediction module executing on the system controller, an estimated walk-away time for the analyzers based upon the test demand and status of the consumable items and maintenance items; displaying an estimated walk-away time for the diagnostic laboratory; and identifying one or more additional actions that are selectable to increase the estimated walk-away time for the diagnostic laboratory.

In a further aspect, a diagnostic laboratory system is provided. The diagnostic laboratory system includes a plurality of analyzers included within the diagnostic laboratory system that are configured to perform tests on samples, wherein each of the plurality of analyzers includes consumable items that are consumed when performing the tests and maintenance items to be performed for continued operation of the analyzers; and a system controller coupled to the plurality of analyzers, the system controller comprising a walk-away time estimation module executable on the system controller, to provide an estimated walk-away time for the plurality of analyzers based upon the test demand and status of the consumable items and maintenance items.

In a yet further aspect, a status visualization method of an analyzer is provided. The status visualization method includes receiving, at a controller of the analyzer, computer-readable data of historical test demand for types of tests and number of the tests to be performed on samples by the analyzer, wherein the analyzer includes consumable items and maintenance items; and determining, via a walk-away time estimation module executing on the controller, an estimated walk-away time for the analyzer based upon the historical test demand and status of the consumable items and maintenance items.

In a further aspect, an analyzer is provided. The analyzer includes a controller of the analyzer including: a test demand module configured to receive computer-readable data of historical test demand for types of tests and number of the tests performed on samples by the analyzer over a previous time period, wherein the analyzer further includes consumable items that are consumed when performing the tests and maintenance items to be performed for continued operation of the analyzer; and a walk-away time estimation module executable on the controller, to provide an estimated walk-away time for the analyzer based upon the test demand estimated from data of historical test demand over a planning period and status of the consumable items and maintenance items.

Still other aspects, features, and advantages of this disclosure may be readily apparent from the following description and illustration of a number of example embodiments, including the best mode contemplated for carrying out the invention. This disclosure may also be capable of other and different embodiments, and its several details may be modified in various respects, all without departing from the scope of the disclosure. This disclosure is intended to cover all modifications, equivalents, and alternatives falling within the scope of the claims.

BRIEF DESCRIPTION OF THE DRAWINGS

The drawings, described below, are for illustrative purposes and are not necessarily drawn to scale. Accordingly, the drawings and descriptions are to be regarded as illustrative in nature, and not as restrictive. The drawings are not intended to limit the scope of the invention in any way.

DETAILED DESCRIPTION

In large diagnostic laboratory systems including a large number of analyzers, it is desirable to increase efficiency as much as possible. When there are several analyzers and possibly other supporting modules (e.g. a sample handler) contained in the diagnostic laboratory, it is a significant challenge for one or even a small number of lab technicians to efficiently replace all the consumable items and perform all the required maintenance items, without having some test stoppages. Thus, in accordance with a first embodiment, a method is provided of determining a WAT for each of those analyzers and supporting modules, and optionally also a smallest WAT for the entire diagnostic laboratory system. If the WAT is visible to lab technician(s), they can focus on other tasks in the diagnostic laboratory without negatively impacting the productivity and the turnaround time of the analyzers. Knowing the WAT improves the productivity and efficiency of the entire diagnostic laboratory process and can minimize work stoppages.

The WAT for each analyzer and supporting module depends on several factors including the samples provided and the ordered and/or expected tests, the fill level of consumable items, and completion of, or status of, the maintenance items of an analyzer or supporting module (e.g., emptying of the liquid and/or solid waste(s)). For each analyzer or supporting module, WAT begins at the time of the last physical touchpoint of the technician with the analyzer or module. While the analyzer or supporting module is running, the WAT is constantly decreasing, until the lab technician must interact with the analyzer or supporting module again (at zero minutes), i.e. to reload or refill one or more consumable items and/or to carry out a maintenance item (e.g., empty solid waste), for example.

In accordance with this disclosure, the term "estimated WAT" for an analyzer is defined as the amount of time that can elapse before a technician must again interface with the analyzer to avoid a testing stoppage. In theory, the estimated WAT for an analyzer or support module can be defined by properties related to the current state of the analyzer or support module (including number of loaded samples, number of assigned tests, fill level of consumables, level of waste, etc.). Thus, in one aspect, an estimated WAT can be visible (e.g., displayed) to the lab technician(s) for one or more of the analyzers and/or support module. Further, a diagnostic laboratory system minimum estimated WAT can also be determined. The minimum estimated WAT for the diagnostic laboratory system can be displayed.

Moreover, in another aspect of the disclosure, knowing the estimated WAT for the analyzer and/or entire diagnostic laboratory system, additional action options can be identified that can be taken to increase the estimated WAT. The additional action options can be based on the current status of the analyzer and/or supporting module of laboratory as a whole. Options may be provided for each analyzer or to lengthen the estimated WAT and for each option, and estimate of how much the estimated WAT can be increased by accomplishing the action option. Furthermore, the system may prompt the technician to confirm completion of the action option once the lab technician selects an action option to complete.

Further, in some embodiments, estimated WAT for an analyzer and/or entire laboratory system may be based on a demand estimate. The demand estimate can be based on historical record data, such as the makeup and number of tests ordered on a particular period in the past that is similar to a current planning period. For example, in diagnostic laboratory systems that have a limited test menu, such as 5-10 tests that can be selected, a good estimate of the breakdown of number and types of tests conducted over a historical period can be used to estimate demand for a like period of time in a later planning period with the same or similar test menu.

These and other features and advantages of the present disclosure describing status visualization methods of a diagnostic laboratory, status visualization methods of an analyzer, and diagnostic laboratory analyzers and systems including WAT estimation modules will be described with reference to FIGS. 1-9 herein.

In accordance with one or more embodiments of the disclosure, a diagnostic laboratory system 100 including multiple analyzers $104_1$-$104_n$ is provided as shown and described with reference to FIG. 1. An analyzer $104_1$-$104_n$ can be any inventory-consuming diagnostic analyzer, such as a clinical chemistry analyzer, immunoassay analyzer, in-vitro analyzer, hematology analyzer, molecular analyzer, or the like. These analyzers $104_1$-$104_n$ can be as described below.

In-vitro analyzer as used herein broadly means any analyzer adapted to conduct tests on samples such as blood, urine, saliva, or the like that have been taken from the human body. An In-vitro analyzer measures a concentration of a specific substance, or analyte (such as sodium or cholesterol), or detects the presence or absence of a particular marker or set of markers, such as a genetic mutation or an immune response to infection, and can be used to monitor a person's overall health to help cure, treat, or prevent diseases. An in-vitro analyzer can conduct tests for hepatitis, HIV, clinical chemistry, coagulation or other blood properties or constituents, urine properties, pregnancy, blood sugar, cholesterol, cancer diagnostics, human genetics, tissue, typing, presence of drugs of abuse or therapeutic drugs, or the like.

Clinical chemistry analyzer as used herein means an analyzer adapted to run assays on samples such as blood serum, plasma, urine, saliva or sputum, cerebrospinal fluid, and the like, to detect the presence of an analyte relating to a disease or a chemical component relating to a drug. Analytes commonly include enzymes, substrates, electrolytes, and specific proteins. Drugs can include drugs of abuse and/or therapeutic drugs. Common clinical chemistry tests includes tests for concentrations of glucose, hemoglobin A1c, sodium, potassium, chloride, lithium, phosphorus, calcium, cholesterol (HDL, LDL), triglyceride, C-reactive protein, bilirubin, lipase, total protein, iron, magnesium, creatinine kinase, urea nitrogen, thyroid stimulating hormone, and the like. Other clinical chemistry tests may be run.

Immunoassay analyzer as used herein means an analyzer adapted to conduct chemical tests used to detect or quantify a specific component in a biological sample using an immunological reaction. Immunoassay analyzers are highly sensitive and specific resulting from the use of antibodies and purified antigens as reagents. Immunoassay analyzers measure the formation of antibody-antigen complexes and detect them via an indicator reaction. High sensitivity is achieved by using an indicator system (e.g., enzyme label) that results in amplification of the measured product. Immunoassays may be qualitative (positive or negative) or quantitative (amount measured). Quantitative immunoassay analyzers measure a signal produced by the indicator reaction.

Immunoassay analyzers can measure (or, in a qualitative assay, detect) an analyte. Immunoassay is a method for measuring analytes present at very low concentrations that cannot be determined accurately by other less expensive tests. Common uses include measurement of drugs, hormones, specific proteins, tumor markers, and markers of cardiac injury, or to detect antigens on infectious agents and antibodies, such as antigens on Hemophilus, *Cryptococcus*, and *Streptococcus* organisms in the cerebrospinal fluid (CSF) of meningitis patients. They are also used to detect antigens associated with organisms that are difficult to culture, such as hepatitis B virus and *Chlamydia* trichomatis, as well as for antibodies produced in viral hepatitis, HIV, and Lyme disease.

Hematology analyzer as used herein means an analyzer adapted to conduct a test on blood, such as a complete blood count (CBC panel), which can include red blood cell (RBC), white blood cell (WBC), hemoglobin concentration, and platelet counts, hematocrit volumes, differential white blood cell counts, red blood cell distribution width, mean corpuscular volume, mean corpuscular hemoglobin, or the like.

Molecular analyzer as used herein means an analyzer adapted to conduct molecular biology methods in molecular biology, biochemistry, genetics; and biophysics that involve manipulation and analysis of DNA, RNA, protein, and/or lipid. In particular, molecular biology analyzers are used to analyze biological markers in the genome and proteome, and can be used to detect infectious disease, in oncology, in human leucocyte antigen typing, coagulation, and pharmacogenomics (e.g., a genetic prediction of drugs that may provide effective therapies).

The diagnostic laboratory system 100 can include any number and mix of the above types of analyzers as analyzers $104_1$-$104_n$. Further, in some embodiments, the diagnostic laboratory system 100 may include a sample mover 106, which may be used to move samples to the analyzers $104_1$-$104_n$.

In particular, diagnostic laboratory system 100 may include a large plurality of analyzers $104_1$ through $104_n$, wherein n is an integer. The number of analyzers $104_1$ through $104_n$ can be one, greater than 1, greater than 3, greater than 6, greater than 10, greater than 20, greater than 50, greater than 100, or even greater than 200 in some embodiments. In some embodiments, one or more sample movers 106, such as an automated track or the like, may be used to transport the samples to be tested to the various analyzers $104_1$ through $104_n$. The sample mover 106 may be configured to transport sample containers containing the samples, such as blood collection tubes (not shown) to and from each of the analyzers $104_1$ through $104_n$ as well as to and from other locations within the diagnostic laboratory system 100. Sample containers may each be provided with one or more labels that may include identification information thereon, such as, a timestamp, sample identification, requested test(s), patient identification, and/or the like. The label(s) may include, e.g., a barcode and/or have alphanumeric information printed thereon. The identification information may be machine readable at various locations about the diagnostic laboratory system 100, so that the location of the sample on the system can be known at all times. The sample mover 106 may be an automated track such as a railed track (e.g., a mono rail or a multiple rail), a collection of conveyor belts, conveyor chains, moveable platforms, or any other suitable type of conveyance mechanism. Automated track may be circular or have another suitable shape and may be a closed track (e.g., an endless track), and may have one or more offshoots or branches with one or more analyzers (e.g., one or more of analyzers $104_1$ through $104_n$) positioned thereon. Carriers may be part of and may operate on the sample transporter 106 to deliver the samples in the sample containers to the various locations on the transportation path of the sample transporter 106.

Figure 1:
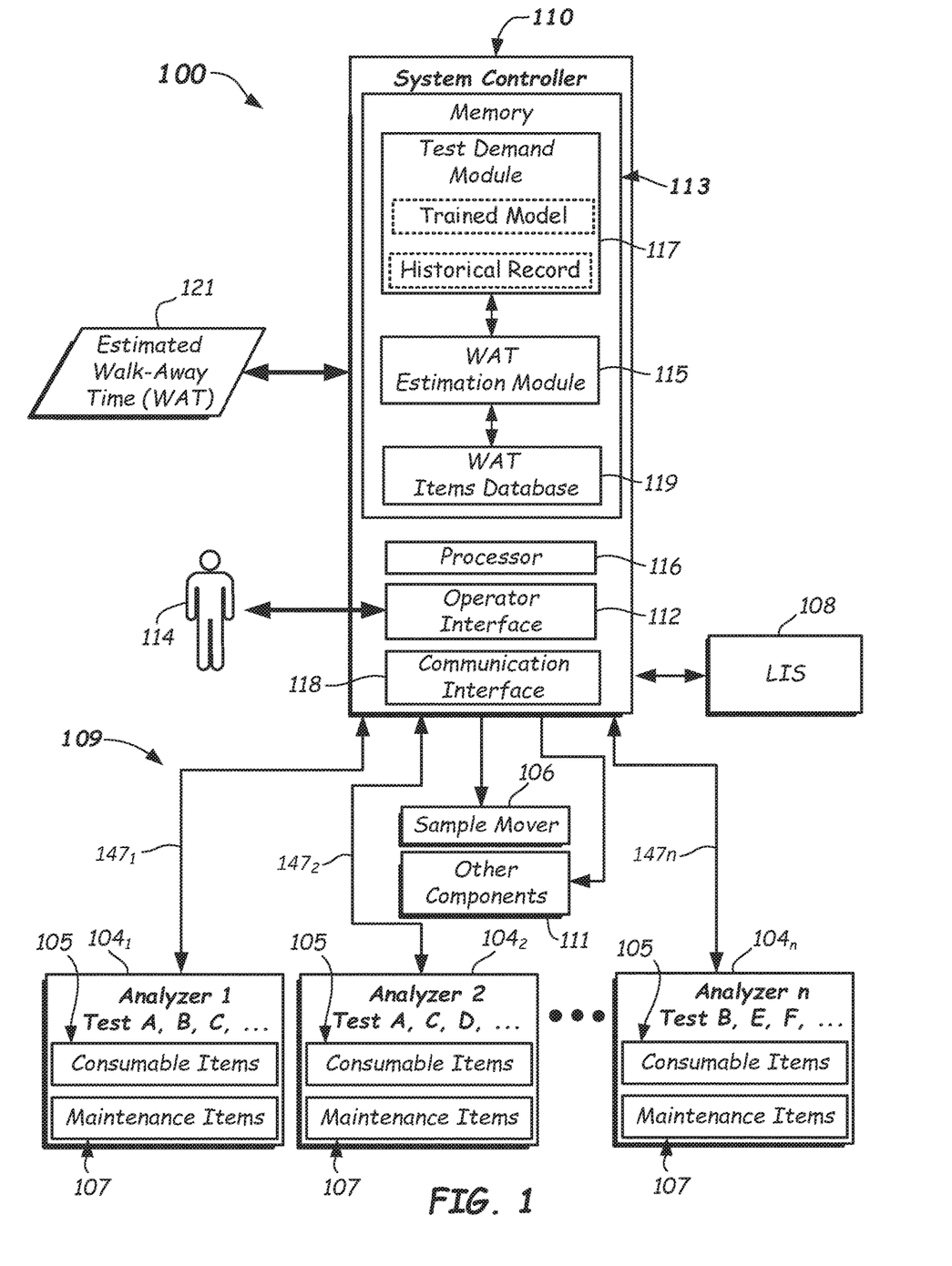
FIG. 1 illustrates a schematic block diagram of a diagnostic laboratory system including a walk-away time (WAT) estimation module according to the disclosure.

The diagnostic laboratory system 100 further includes, as shown in FIG. 1, a system controller 110 that is configured and operable to carry out the status visualization method for the diagnostic laboratory system 100 and provide, as an output, an estimated walk-away time (WAT) 121 for the diagnostic laboratory system 100 and/or for one or more or all of the analyzers $104_1$-$104_n$ in the diagnostic laboratory system 100. If subject to maintenance items, the sample mover 106 may also include an estimated WAT, which may be calculated.

Each of the analyzers $104_1$-$104_n$ in the diagnostic laboratory system 100 are configured to perform tests on samples, wherein each of the tests may be selected from a menu of tests established for each analyzer. The test menus for each of the analyzers may be different. Some of the tests may be the same, such as for tests that are in high demand. Each of the plurality of analyzers $104_1$-$104_n$ includes consumable items 105 that are consumed when performing the tests that are selected from the test menus. Furthermore, each of the plurality of analyzers $104_1$-$104_n$ includes maintenance items 107 to be performed to provide continued operation of the analyzers $104_1$-$104_n$.

The consumable items 105 for each analyzer $104_1$-$104_n$ can include, but are not limited to, any material or devices that are consumed as a part of running the tests on the analyzers $104_1$-$104_n$. For example, the consumable items 105 can include, but are not limited to, one or more of test-specific reagents, bulk reagent, calibrators, conditioner, control liquids (QC liquids), diluent, wash liquid, pipette tips, and reaction vessels. Maintenance items 107 associated with each of the plurality of analyzers $104_1$-$104_n$ can include emptying of solid waste and/or liquid waste. If other maintenance items are scheduled to be accomplished, then they may also be included.

The diagnostic laboratory system 100 can further include a system controller 110 that is coupled to the plurality of analyzers $104_1$-$104_n$ such as through a suitable communication network 109. Communication network 109 may be any suitable communication network that allows electronic data communication between the system controller 110 and the respective plurality of analyzer s $104_1$-$104_n$. The diagnostic laboratory system 100 can further include communication between the system controller 110 and one or more sample movers 106 such as through the suitable communication network 109.

As shown, system controller 110 includes a memory 113 (e.g., RAM, ROM, other memory devices, or combinations thereof) configured to receive and store programming instructions and other information/data that is used to estimate WAT for each analyzer, sample mover 106, and/or for the diagnostic laboratory system 100. System controller 110 may also include a processor 116 (e.g., a CPU, microprocessor, or other like processing device) configured to execute programming instructions. System controller 110 may further include a communication interface 118, which may enable the system controller 110 to be coupled to, and in electronic communication with, laboratory information system (LIS) 108, sample mover 106, one or more other components 111 such as various sensors, barcode readers, robotic mechanisms, sample container loading and/or unloading area, pre-processing station (which may include, e.g., an automated centrifuge and sample pre-screening modules, such as for screening for Hemolysis, Icterus, and Lipemia (HIL), or other artifacts such as bubbles, clots, foam), decapper, aliquotter, and the like, and analyzers $104_1$ through $104_n$ so that data and/or information may be communicated there between. In some embodiments, communication interface 118 may enable communication over a communication network 109. Communication interface 118 may interface and communicate with the various analyzers $104_1$ through $104_n$ by way of communication channels $147_1$ through $147_n$.

Communication channels $147_1$ through $147_n$ may be part of a communication network 109 enabling data communication between the system controller 110 and the various workstations or computers associated with each analyzer $104_1$ through $104_n$. The communication network 109 may in some embodiments include, e.g., the internet where system controller 100 may be operable as a cloud-based server or the like, a local area network (LAN), wide area network (WAN), a wireless local area network (WLAN), a power line communication (PLC) network, or the like. System controller 110 may include an operator interface 112 that may be configured to receive input data from an operator such as a lab technician 114 relating to the various operating modules used to carry out the WAT estimation or estimations. In the case of the system controller 100 being cloud-based, the operator interface 112 may include a system component such as a work station, tablet, local computer, or server, which can be used to locally provide data input and receive the estimated WAT 121 from the cloud server. Operator interface 112 may include a keyboard, mouse, touchscreen, or other manipulated device for data input and instructions.

The system controller 110 may further comprise a walkaway time estimation module 115 that is stored in memory 113 and comprised of programming code executable on the processor 116 of the system controller 100, to provide an estimated WAT 121 for one or more of the analyzers $104_1$-$104_n$, for each of the analyzers $104_1$-$104_n$, and/or a minimum WAT for the diagnostic laboratory system 100 in its entirely. The estimated WAT in each case is based upon the test demand as well as on the status of each of the consumable items 105 and maintenance items 107.

In the present diagnostic laboratory system 100 and methods described herein, details concerning the workload (demand) taking place within the diagnostic laboratory system 100, such as information about the number of samples and the requested tests on each sample can be available from a test demand module 117. Test demand module 117 may receive and generate estimated test demand based upon:

1) input from the lab technician 114,
2) input received from the one or more analyzers $104_1$-$104_n$,
3) input from the LIS 108, and/or
4) input from historical record of test demand.

In more detail, test demand module 117 can predict an estimated test demand over a selected planning period. Test demand estimation can be based on test information input by the lab technician 114, which may be an estimate of the test demand based on knowledge of the lab technician 114 on the makeup of daily testing in terms of number of tests run from each test option on the test menu for an analyzer $104_1$-$104_n$. Further, test information may be an estimate of the test demand based on actual test runs to be conducted by the analyzers $104_1$-$104_n$. Further, test information may be an estimate of the test demand based on actual test order data received from the LIS 108, such as the tests to be conducted over a planning period, such as a half shift, shift, or longer. In some embodiments, test information may be an estimate of the test demand based on stored historical data, such data from each of the analyzers $104_1$-$104_n$ over a suitably-similar time period in the past, such as a shift, day, week, month or the like.

Test demand estimation used to determine estimate WAT can be a subset of a larger dataset, such that test demand estimation considers only a limited time frame (e.g., a planning period). Planning period is the time period over which the WAT estimation is run, and can be user selectable. In general, the WAT estimation is run by the WAT estimation module 115 over a planning period which is shorter than or equal to the time length of available test information.

Figure 2:
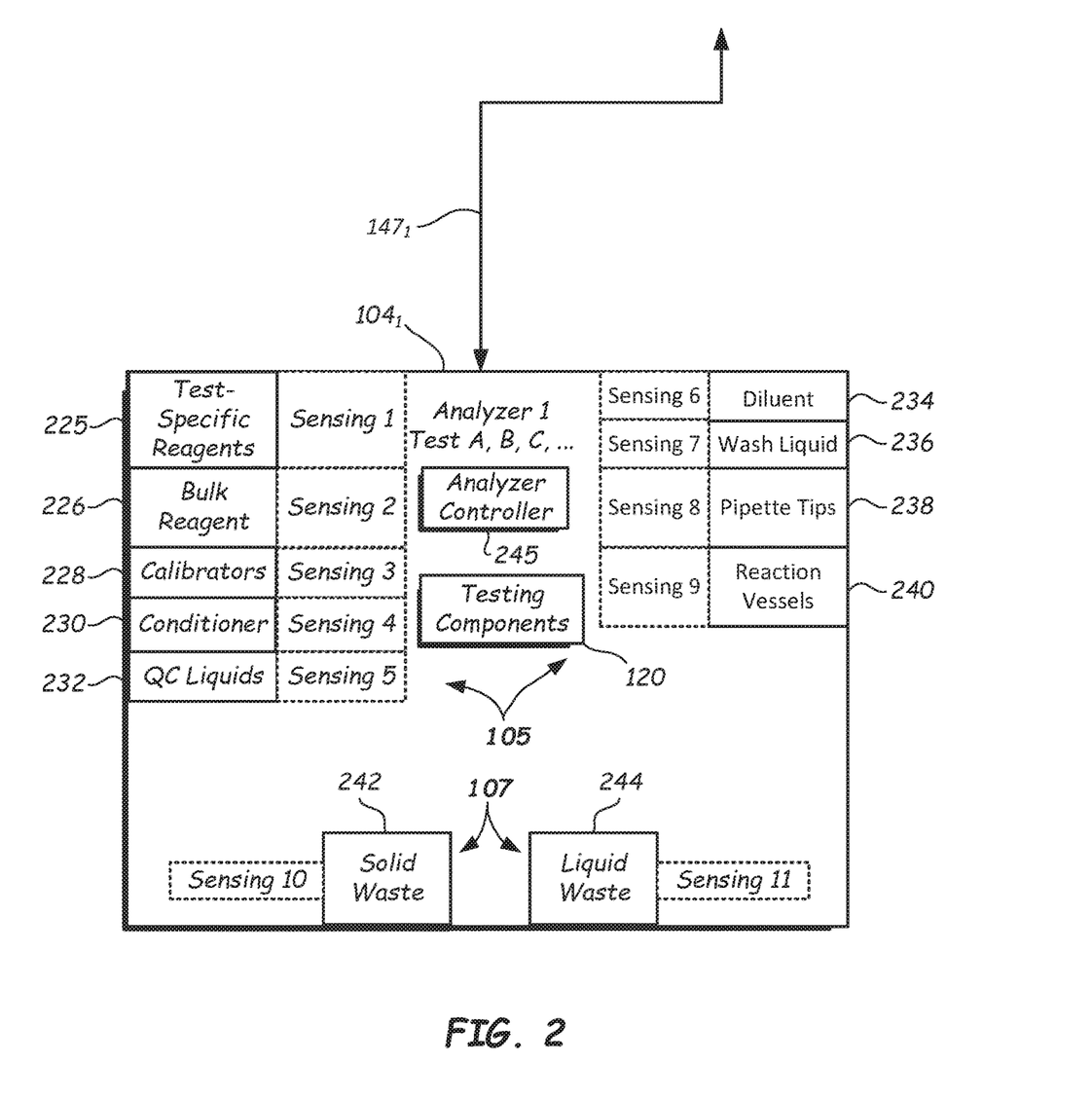
FIG. 2 illustrates a schematic diagram of a representative analyzer including consumable items used in testing and maintenance items that are conducted to enable continued testing according to the disclosure.

As is illustrated in FIG. 2, each of the analyzers $104_1$ through $104_n$ (analyzer 1—$104_1$ shown as a representative example) can contain or have associated therewith some type of reagent pack holder that is configured and adapted to hold reagent packs, which contain one or more test-specific reagents 225. Other reagent packaging can be used. The reagent pack holder can have a configuration suitable to the particular type of analyzer. Each reagent pack holder can include multiple mounting spaces that are configured to receive a reagent pack thereat. Mounting spaces may have any suitable configuration designed to receive a reagent pack thereat, and may be a slot, recess, or groove, or any other suitable mounting structure. There may be various types of reagent packs that can be loaded onto the mounting spaces and they may have one test-specific reagent therein, such as the same reagent in all reservoirs thereof, or any number of test-specific reagents or other liquids therein. Some reagent packs can contain ancillary reagents, which are also considered test-specific reagents herein. The number and mix of types of test-specific reagents 225 to be placed on each analyzer $104_1$ to $104_n$ is determined by the estimate of test demand, i.e., an estimate of a number of each test to be conducted over the planning period, as disclosed herein.

Analyzer 1—$104_1$ shown can contain or have associated with it consumable items 105, such as one or more of bulk reagent 226, calibrators 228 that may be specific to each test type, conditioner 230, and QC liquids 232, which also may be specific to each test type, diluent 234, wash liquid 236, pipette tips 238, and reaction vessels 24 (e.g., cuvettes, cartridges, or well plates). Other consumable items 105 may include one or more allergens, reaction triggering materials, detection chips, buffer liquids, and/or suspensions of magnetic particles (beads) or other coated beads that are used on some analyzers. These types of consumable items 105 are filled as needed by the operator 114. Knowing which of the consumable items 105 needs to be refilled first as well as what the WAT is for a particular analyzer or the diagnostic laboratory system as a whole is very helpful to the lab technician 114 to ensure continuous operation and avoiding work stoppages.

Again referring to FIG. 2, the analyzer $104_1$ shown may include one or more maintenance items 107. Maintenance items 107 can include, for example, emptying solid waste 242, and/or emptying liquid waste 244. Solid waste 242 can include used pipette tips 238 and/or used reaction vessels 240. Liquid waste 244 can include used test liquids, such as wash liquid 236 or other liquids used in the testing.

Shown next to each of the consumable items 105 and maintenance items 107 are sensing 1-11. "Sensing" as used herein denotes that for some or all of the consumable items 105 and/or maintenance items 107, some form of measurement or count is provided so that a status of the particular consumable items 105 and/or maintenance items 107 can be determined. For example, in one embodiment, the sensing may be provided by a count, such as an integer count. For example, if one test-specific reagent 225, as packaged, can be used to conduct twenty of that specific test, then a count of from 1 to 20 may be generated. Based on how many tests have already been conducted, a count of how many tests can still be conducted without replacing the reagent pack or other packaging of the test-specific reagent 225 can be generated. Thus, based on the estimated test demand for the analyzer $104_1$, and the particular status of the particular consumable item, a WAT estimate can be calculated for that test-specific reagent 225 based on the number of counts remaining, the time it takes to conduct that specific test, and the order of all other tests, calibrations, and QC tests within the planning period. Thus, a WAT estimate for that particular test specific reagent 225 can be determined and displayed, such as on a WAT status screen (See FIG. 4).

Analyzer controller 245 further can electronically communicate with the system controller 110, as indicated by communication channel $147_1$, which may be a wired or wireless communication channel. The communication may be a count of remaining tests that can be conducted on a particular test-specific reagent 225. Likewise, the sensing may be provided from a suitable sensing device, such as a depth or height sensor to measure an amount of a liquid remaining. For example, a depth may be determined based on a capacitive, laser, or other distance measuring sensor implemented as part of a pipette that is configured to aspirate and dispense a test-specific reagent 225, calibrator 228, conditioner 230, QC liquid 232, or other liquid. Based on a known starting height or depth, and amount of remaining liquid can be determined and communicated through communication channel $147_1$. In the case of maintenance items 107, such as solid waste 242 or liquid waste 244, weight sensing may be provided to determine a percentage of full, such as with a load cell or the like. Other forms of sensing may be used, such as a count of a number of tests that can be conducted before emptying of the solid waste 242 or liquid waste 244 is needed. Optionally, a broken beam sensor may be used. Some or all of the other analyzers $104_1$ to $104_n$ may also communicate the status of the various consumable items 105 and maintenance items 107 to the system controller 110. The particular analyzer controllers 245 of some or all of the analyzers $104_1$ to $104_n$ may store the status of the various consumable items 105 and maintenance items 107 and communicate to the system controller 110 at any suitable sampling rate, such as at every sensing update, every few sensing updates, after each test, or after a certain time period, or the like. Thus, the system controller 110 can have stored in memory 113, a running tally of the status of each of the consumable items 105 and maintenance items 107 for some or all of the analyzers $104_1$ to $104_n$ that can be accessed for determining an estimated WAT 121 by the WAT estimation module 115.

Figure 3:
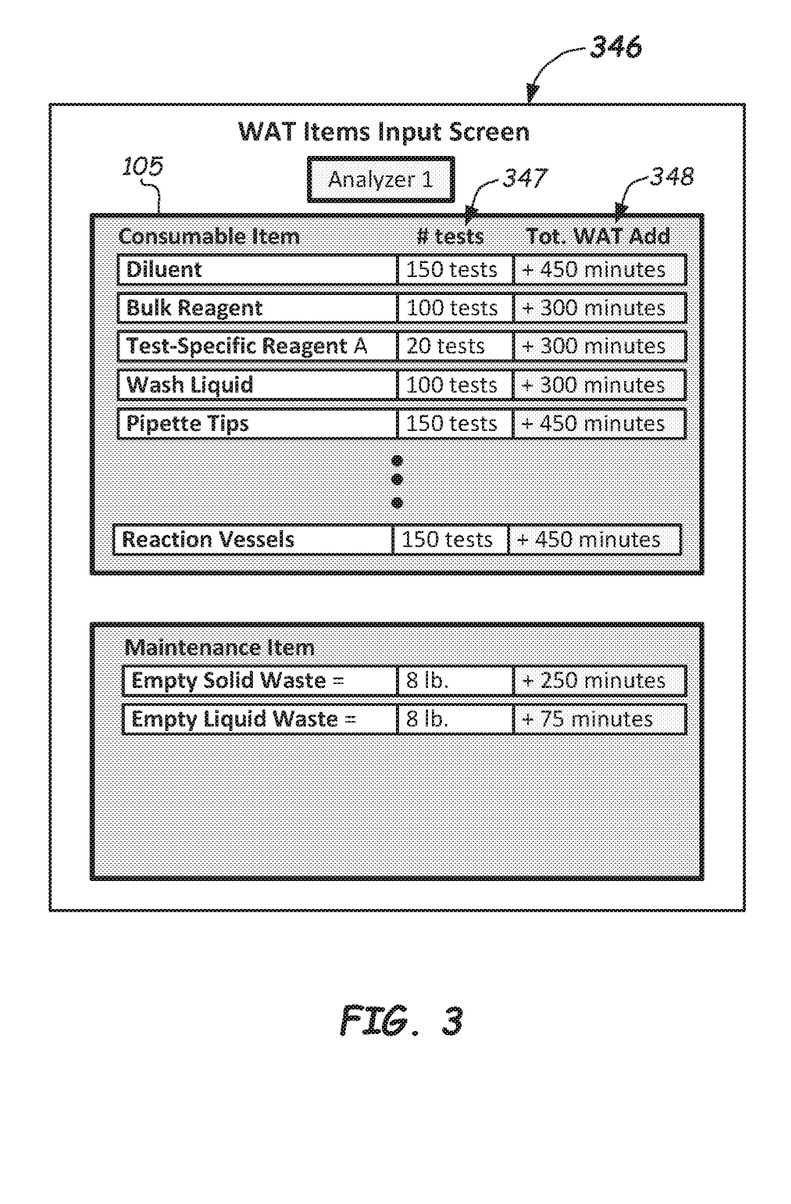
FIG. 3 illustrates an example schematic diagram of a WAT items input screen according to the disclosure.

Now referring to FIG. 3, the system controller 110 can include a WAT items database 119 stored in memory 113 and which is accessible by the WAT estimation module 115. The WAT items database 119 can include specific times associated with each consumable items 105 and maintenance items 107 for some or all of the analyzers $104_1$ to $104_n$. For example, as shown for analyzer 1, the WAT items input screen 346 includes a number of consumable items and maintenance items 107 that can have various inputs. For example, for the analyzer 1 $104_1$, the lab technician 114, programmer, or other person setting up the WAT estimation method can input various inputs via operator interface 112, such as the number of tests 347 that a particular consumable item 105 will last, and/or the total WAT Add 348, which may be based on the time to carry out each of the specific tests. If all the tests conducted using the particular consumable item 105 have the same length then the WAT Add 348 can be easily determined. However, if the specific tests in the test menu for an analyzer (e.g., analyzer 1 $104_1$) have different lengths, then the WAT Add 348, can be a calculated based on the sum of the times to run the applicable number of tests based on the particular estimated test demand over the planning period. Thus, in the case of tests on the menu having different time lengths, the test demand will adjust the value of the total WAT add 348. Similar inputs may be made for the maintenance items 107. As shown, the maintenance items are based on weight, but they could be based on test counts as well. Some or all of the analyzers $104_1$ to $104n$ can include a WAT items input screen 346.

Figure 4:
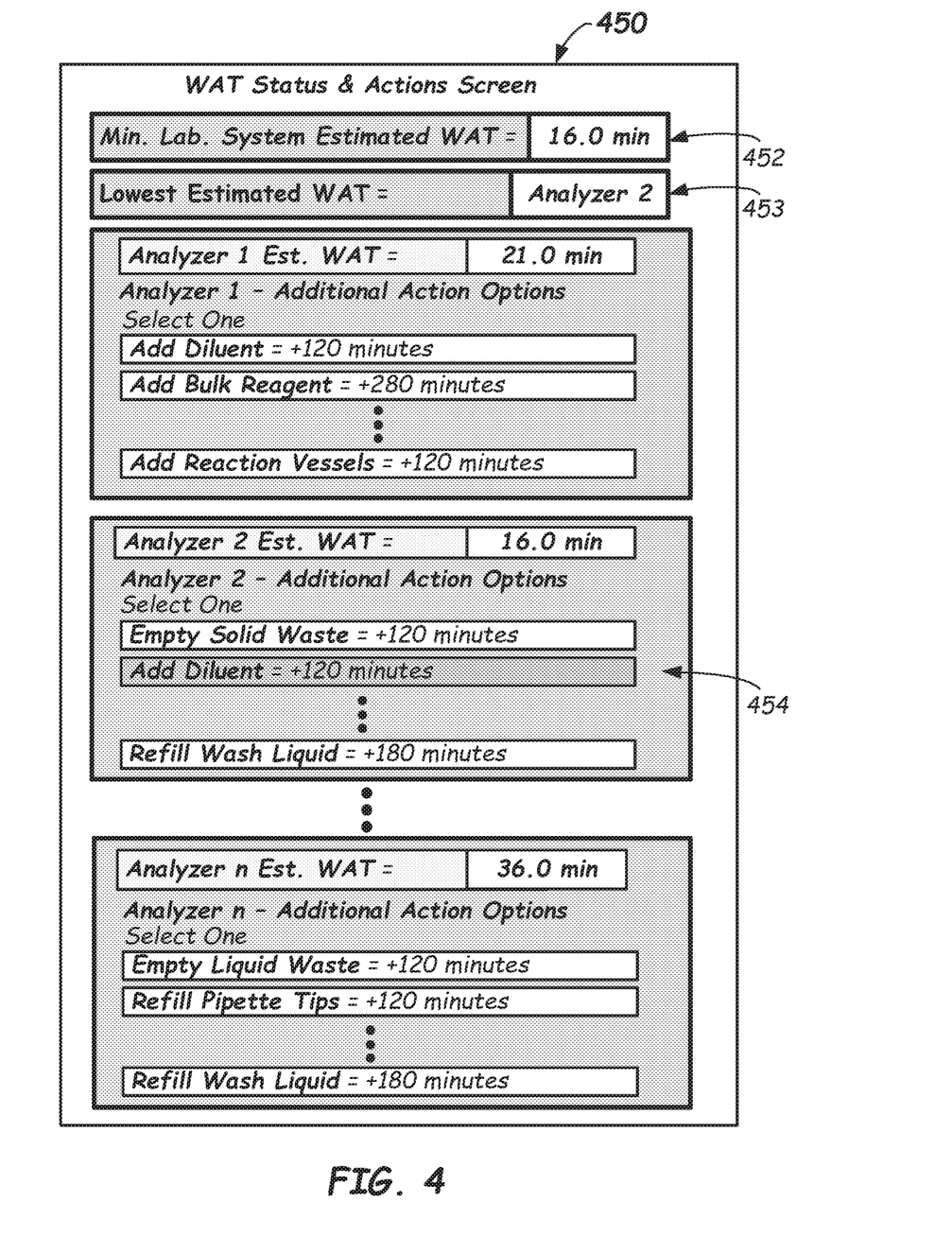
FIG. 4 illustrates an example schematic diagram of a WAT status and actions screen for analyzers of the diagnostic laboratory system according to the disclosure.

Thus, the WAT estimation module 115 calculates and determines an estimated WAT for some or all of the analyzers $104_1$ to $104_n$, such as shown in the WAT status and actions screen 450 of FIG. 4. WAT status and actions screen 450 can display the particular analyzer that has the lowest WAT, which is the minimum laboratory system WAT. In the example shown, Analyzer 2 $104_2$ has a 16.0 minute WAT, and thus is determining the minimum laboratory system estimated WAT 452 for the diagnostic laboratory system 100. The analyzer having the minimum laboratory system estimated WAT 452 can also be displayed at block 453. Each of the analyzers can be displayed on WAT Status and actions screen 450 so that the lab technician 114 can quickly gauge actions to take to lengthen the minimum laboratory system estimated WAT 452.

Figure 5:
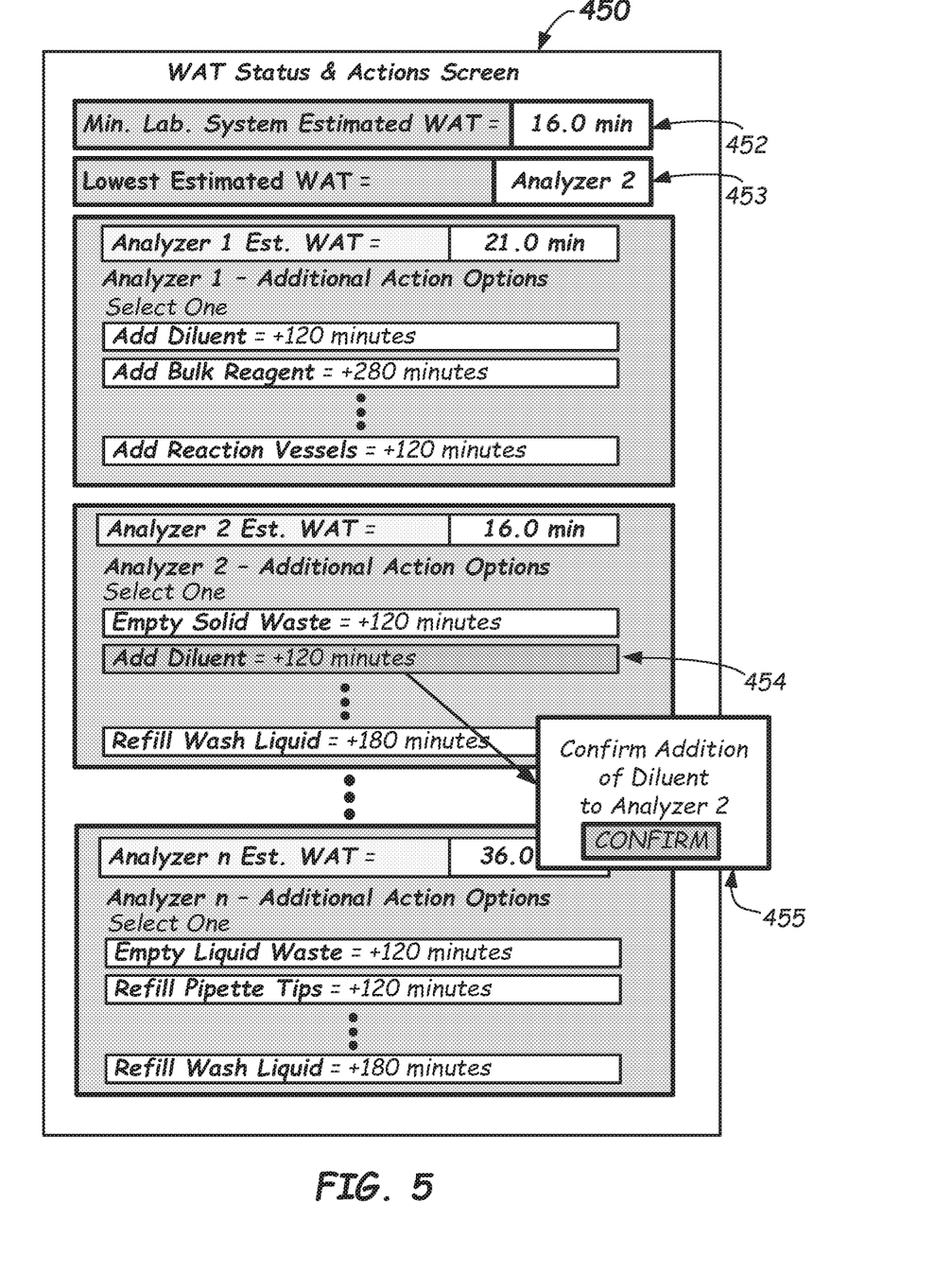
FIG. 5 illustrates an example schematic diagram of a WAT status and actions screen for analyzers of the diagnostic laboratory system with an additional action selected and providing confirmation of the selection according to the disclosure.

FIG. 5 illustrates a WAT status & Actions screen 450 wherein a user, such as lab technician 114, has selected an additional action option (Add Diluent) from a list of available action options 454. The selection can be made from the list additional action options 454 and one or more of the action options may be highlighted as being the action option that has resulted in the minimum laboratory system estimated WAT 452 for the identified analyzer 453. Another option may be alternatively selected, but may not raise the minimum laboratory system estimated WAT 452. As shown, selection of the "Add Diluent" action option, such as from a populated list, adds an amount of time to the minimum laboratory system estimated WAT 452. It may not add the full amount listed, as another consumable item 105 or maintenance item 107 may now become the limiting item.

However, the listed addition +120 minutes will be added to the time for that action item, so that based on the test demand for the planning period, the "Add Diluent" will not have to be revisited for that amount of time.

As shown, when the lab technician 114 selects an action item from the list of action items 454, and as the selected action option from the list of action items 454 is completed, the new status of the consumable item 105 and/or maintenance item 107 can automatically be sensed by any suitable sensing mechanism or process. In this case, the WAT for that item is confirmed automatically.

Alternatively, a confirmation selection 455 can be initiated, such as by a pop-up window or other suitable interactive confirmation selection. When the technician 114 has completed the selected action option from the list of action items 454, they can select "CONFIRM" from the confirmation selection 455. This then causes the WAT estimation module 115 to recalculate the minimum laboratory system estimated WAT 452, and set the count or other measure for the selected action item (e.g., Add Diluent") to the maximum value, where it will now continue its countdown for every time the Diluent is used in a test for the analyzer. Further, once the "CONFIRM" selection is made, WAT estimation module 115 can identify on the WAT Status & Actions Screen 450 the analyzer at block 453 that now has the new minimum laboratory system estimated WAT 452. Further, the WAT estimation module 115 can now highlight or otherwise identify an action item from the list of action items 454 of an analyzer that is the action item that needs to be next addressed which is causing the new minimum laboratory system estimated WAT 452.

Figure 6:
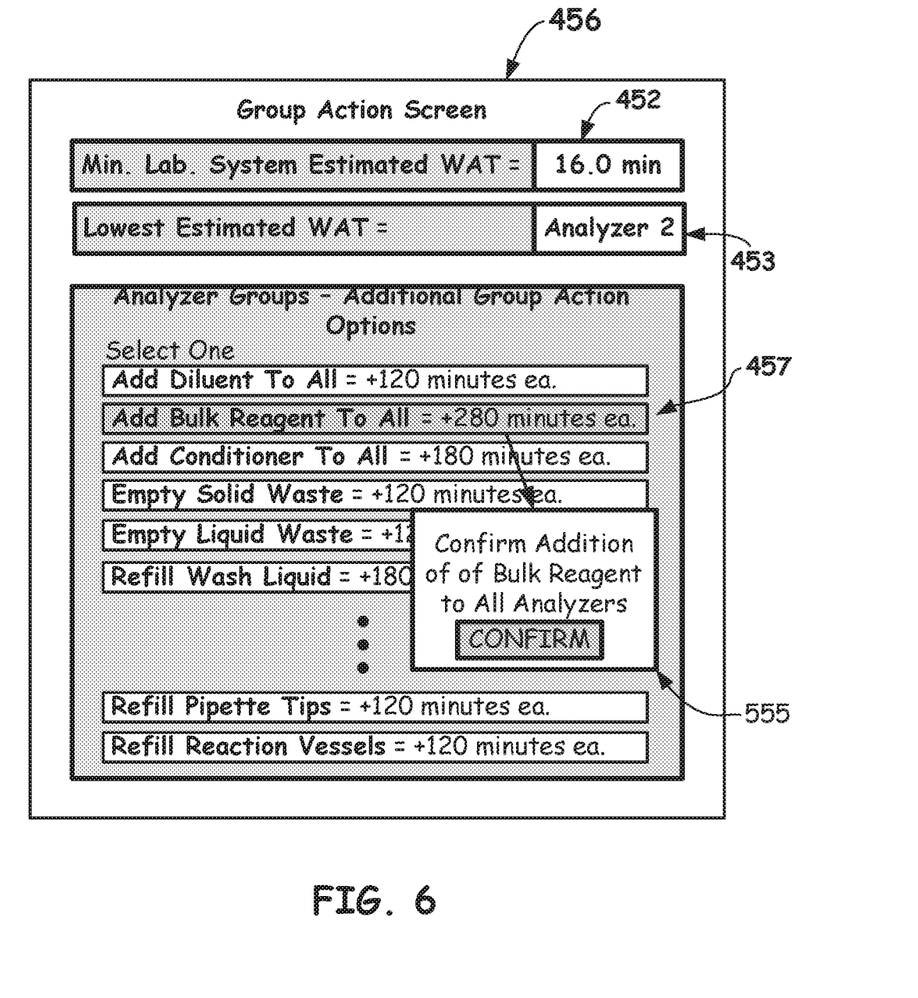
FIG. 6 illustrates an example schematic diagram of a group action screen for analyzers of the diagnostic laboratory system with an additional group action selected according to the disclosure.

FIG. 6 illustrates a group action screen 456 wherein a user, such as lab technician 114, can select an additional group action option from a list of available additional group action options 457. The selection can be made from the list additional group action options 457 and one or more of the group action options may be highlighted or otherwise indicated as being the group action option that has resulted in the minimum laboratory system estimated WAT 452 for the identified analyzer 453. The user may select the highlighted action option and that option will result in extending the minimum laboratory system estimated WAT 452 for the diagnostic laboratory system 100. In this case, the group action option "Add Bulk Reagent To All" was highlighted, indicating it was the particular consumable item 105 that was to be in need of replenishment first. As shown, selection of this group action option will add (+) 280 minutes to the bulk reagent, which is consumable item 105. Thus, depending on current demand, the time for next needing to address the consumable item is extended by the estimated amount. Again a pop-up or other user-selectable confirmation item may be used for the user (e.g., lab technician 114) to CONFIRM that the selected group action option has been completed on all analyzers $104_1$-$104_n$. Once confirmed by user via selecting the CONFIRM selection via clicking with a mouse or via a touchscreen, this causes the WAT estimation module 115 to recalculate the minimum laboratory system estimated WAT 452, and set the count or other measure for the selected group action option (e.g., Add Bulk Reagent To All") to the maximum value, where it will now continue its countdown for every time the bulk reagent is used in a test for the analyzer. Further, once the "CONFIRM" selection is made, WAT estimation module 115 can identify, on the WAT Status & Actions Screen 450, the analyzer at block 453 that now has the new minimum laboratory system estimated WAT 452. Further, the WAT estimation module 115 can now highlight or otherwise identify a new group action option from the list of additional group action options 457 of an analyzer that is the action option that needs to be next addressed, which is causing the new minimum laboratory system estimated WAT 452.

Figure 8:
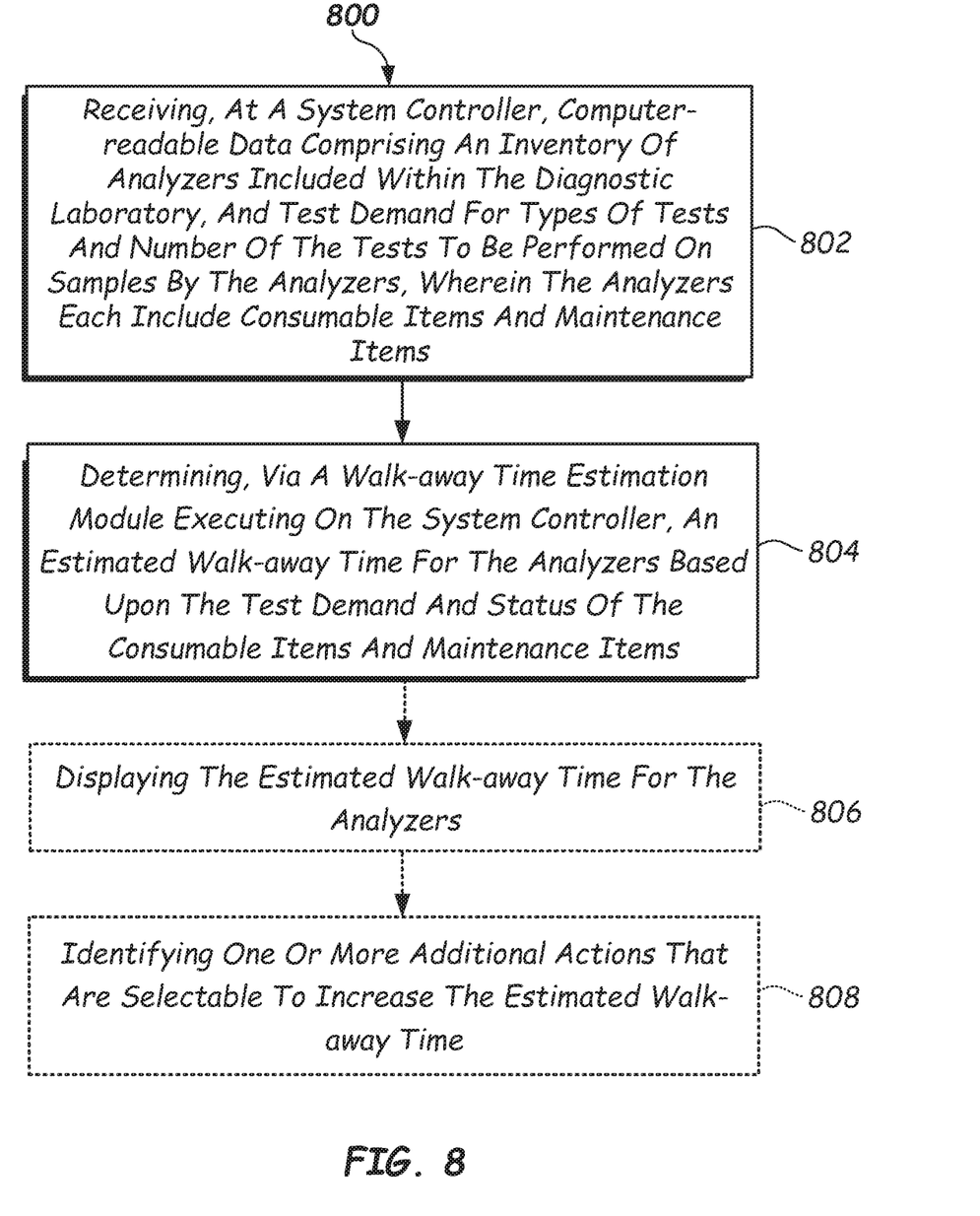
FIG. 8 is flowchart of a status visualization method of a diagnostic laboratory according to the disclosure.

FIG. 8 illustrates a flowchart of a status visualization method 800 of a diagnostic laboratory system 100 according to one or more embodiments of the disclosure. Status visualization method 800 may be carried out by a suitable system controller, such as, e.g., system controller 110, or other suitable computer device. Status visualization method 800 may include, at process block 802, receiving, at the system controller (e.g., system controller 110), computer-readable data comprising an inventory of analyzers (e.g., analyzers $104_1$ through $104_n$) included within the diagnostic laboratory system, and test demand for types of tests and number of the tests to be performed on samples by the analyzers. Test demand can be received from the test demand module 117. The analyzers (e.g., analyzers $104_1$ through $104_n$) each include consumable items (e.g., consumable items 105) and maintenance items (e.g., maintenance items 107).

The method 800 includes, in block 804, determining, via a walk-away time estimation module (e.g., walk-away time estimation module 115) executing on the system controller (e.g., system controller 110), an estimated walk-away time (e.g., estimated walk-away time 121) for the analyzers based upon the test demand and status of the consumable items and maintenance items. The status of the consumable items (e.g., consumable items 105) and maintenance items (e.g., maintenance items 107) can be provided by sensing as described herein. Sensing may be provided by a test count or by physical measurement of liquid depth, height, volume, pressure, proximity, or the like. The estimated walk-away time 121 can be the minimum WAT from all of the analyzers $104_1$ through $104_n$.

The method 800 can include, in block 806, displaying the estimated WAT 121 for the analyzers $104_1$ through $104_n$. This can, in one embodiment, mean displaying a WAT for each of the analyzers $104_1$ through $104_n$ as in FIG. 4. In another embodiment, it can mean displaying the minimum laboratory system estimated WAT 452 as shown on the WAT status & actions screen 450 of FIG. 4.

The method 800 can further include, in block 808, identifying one or more additional actions that are selectable to increase the estimated walk-away time (WAT) as shown in FIG. 5.

Figure 7:
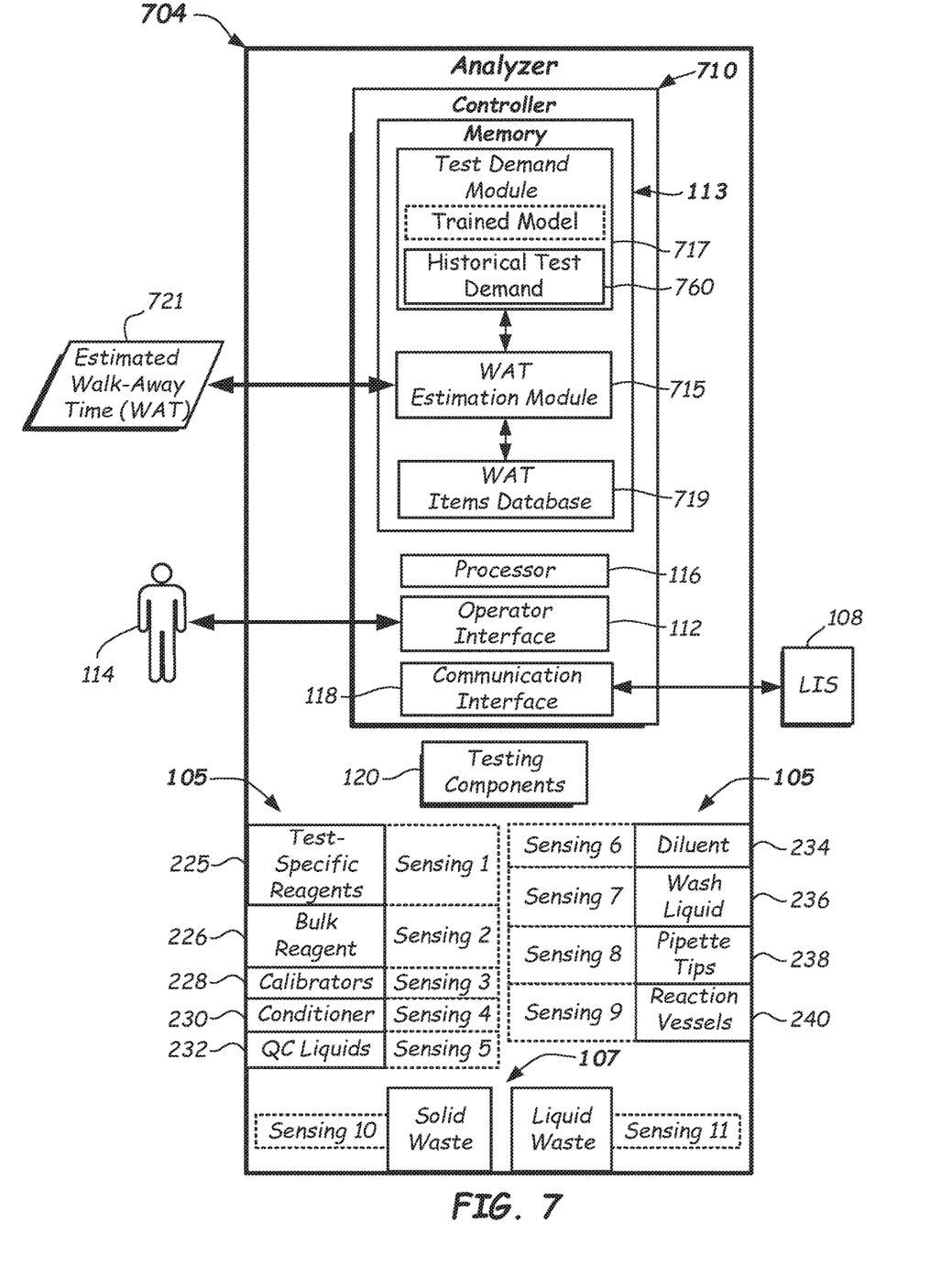
FIG. 7 illustrates a schematic block diagram of an analyzer including a walk-away time (WAT) estimation module taking into account historical test demand information according to the disclosure.

FIG. 7 illustrates an example embodiment of an analyzer 704 that is configured to carry out testing on samples. Analyzer 704, depending on the type of analyzer, includes conventional testing components 120, such as loading racks, pipette(s), pipette robot(s), incubation members (e.g., incubation rings), reagent carousel or trays, aspiration and dispensing pumps and associated hardware, cuvette loaders, heaters, readers for chemiluminescence, fluorescence, or the like. In particular, the analyzer 704 includes a WAT estimation module 115 that can generate and display an estimated walk-away time (WAT) 721 for the analyzer 704. In particular, the analyzer 704 can include a controller 710 including a test demand module 717 and a WAT estimation module 715, which are software modules that can be stored in memory 113 and executable on processor 116. Test demand module 717 is configured to receive computer-readable data of historical test demand 760 for types of tests and number of the tests performed on samples by the analyzer 704 (or another analyzer with a same test menu) over a previous time period. Such computer-readable data of historical test demand 760 can be stored as the testing is conducted over the previous time period. The period for data storage should be sufficiently long, so that the user can select a planning period of equal of less length than the previous time period. As before, the analyzer 704 includes consumable items 105 that are consumed when performing the tests and maintenance items to be performed for continued operation of the analyzer 704. The walk-away time estimation module 715 can be executable on the controller 710, to provide an estimated walk-away time 721 for the analyzer 704 based upon the test demand estimated from previously-stored data of historical test demand 760 over the selected planning period as well as on the status of the consumable items 105 and maintenance items 107.

As described previously, some or all of the consumable items 105 and maintenance items 107 can include entries in the WAT Items database 119 of the amount of time that it takes to deplete all of the particular consumable items 105 and/or to conduct the maintenance item 107. Readings of each of the sensings (e.g., sensing 1-11 shown) may provide continuous updates on the status of the particular consumable items 105 and/or maintenance items 107. The sensings may be provided as test counts, when the measure is how many tests can be conducted for a particular consumable item 105 and/or maintenance items 107. Optionally, sensings can be provided by any suitable sensor, such as a depth, height, weight, proximity, or other sensor that can provide a sensing of a status of particular consumable item 105 and/or maintenance items 107. Status may be provided in any useful measure, such as % remaining, % used, a fraction of tests conducted/total tests possible before replenishment (e.g., 144/150), or other suitable status indicator.

Walk-away time estimation module 715 determines the estimated WAT 721 for the analyzer 704 by using the tests estimated to be conducted over the selected planning period, wherein the test makeup and test time for each test is actually recorded in the data of the historical test demand 760. However, the selected planning period may be less than the total amount of data available. For example, if the user selects a day as the applicable planning period, and a week's worth of data is available, the walk-away time estimation module 715 may use a like day to provide the demand estimate (e.g., Tuesday), or optionally, can average for the numbers and makeup of tests over a longer period of the historical data. The planning period can be any suitable period, such as a shift, a day, a week, or other suitable time and may be selectable by the user (e.g., lab technician), or can be a fixed period. Based on the estimated test number and test makeup over the planning period obtained from the test demand module 717, as well as previous the input from the WAT items database 719, and the current status of the consumable items 105 and maintenance items 107, a WAT can be determined for each of the consumable items 105 and maintenance items 107. Selecting the least from the group of WATs then provides the minimum estimated WAT 721 and identifies the consumable item 105 or maintenance item 107 that has the minimum estimated WAT 721.

Figure 9:
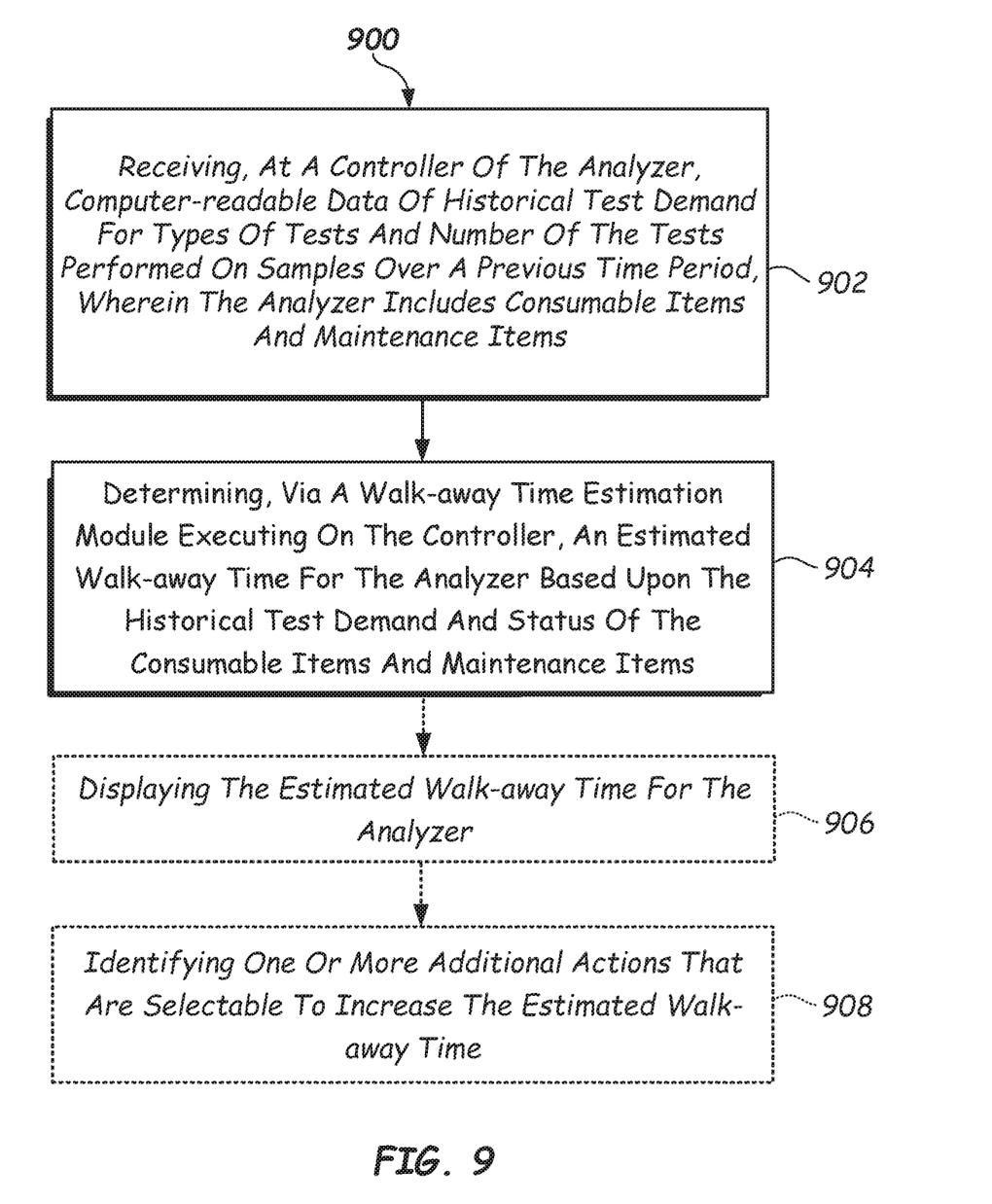
FIG. 9 is flowchart of a status visualization method of an analyzer according to the disclosure.

FIG. 9 illustrates a flowchart of a status visualization method 900 of an analyzer (e.g., analyzer 704) of a diagnostic laboratory system 100 according to one or more embodiments of the disclosure. Status visualization method 800 may be carried out by a suitable controller, such as, e.g., controller 710, or other suitable computer device. Status visualization method 800 may include, receiving, at a controller of the analyzer, computer-readable data of historical test demand for types of tests and number of the tests performed on samples (e.g., by the analyzer 704 or another analyzer having a same test menu) over a previous time period, wherein the analyzer includes consumable items and maintenance items (e.g., consumable items 105 and maintenance items 107).

The method 900 further includes, in block 904, determining, via a walk-away time estimation module (e.g., walk-away time estimation module 715) executing on the controller, an estimated walk-away time (e.g., an estimated walk-away time 721) for the analyzer based upon the historical test demand over the planning period and status of the consumable items and maintenance items (e.g., consumable items 105 and maintenance items 107).

The method 900 can include, in block 906, displaying the estimated WAT 121 for the analyzer 704. The method 900 can further include, in block 908, identifying one or more additional actions that are selectable to increase the estimated walk-away time (WAT).

The historical test demand over a selected planning period may be provided from the test demand module 717, which can provide the test demand for the planning period based on historical test data 760 stored in memory 113. For example, if the planning period is a day, then the test demand estimation can be based on a like day stored in memory 113. If the planning period is a week, then the test demand estimation can be based on a like week stored in memory 113. Optionally, the test demand over the selected planning period may be provided from a trained model of the test demand module 717 stored in memory 113 and executable on the processor 116. The trained model may include historical data and also various intricacies of the specific laboratory, such as test menus for a specific time of year, operations or changes in demand that are specific to a particular analyzer or group of analyzers over a particular period of time, such as changes in demand from fall to winter due to the flu, changes in demand due to increased demand for certain test types over time, changes in test demand on particular days, and the like.

The test demand module 717 may look back over a period of time in the past and can use the average consumption of materials within a specific laboratory to predict today's needs over the planning period. It's also possible to use some number of specific days, like an average of a number of like days, such as an average of the last six Tuesdays, since the laboratory system may have different test demand and a different makeup of tests on different days of the week. Some trained models may take into account factors that are external to the laboratory system such as flu season, allergy season, or specific outbreaks of particular diseases in estimating demand. Those kinds of factors that can affect test demand can vary from year to year, so the demand input may need to come from larger real-time data pools such as averaging across several diagnostic laboratory systems, such as in a region, or relating to information on illnesses from hospital intakes or CDC reports, or other ancillary information that can affect test demand.

While the disclosure is susceptible to various modifications and alternative forms, specific method and system embodiments have been shown by way of example in the drawings and are described in detail herein. It should be understood, however, that the particular methods and systems disclosed herein are not intended to limit the disclosure but, to the contrary, to cover all modifications, equivalents, and alternatives falling within the scope of the claims.

What is claimed is:

1. A status visualization method of a diagnostic laboratory system, comprising:

receiving, at a system controller, non-transitory computer-readable data comprising an inventory of analyzers included within the diagnostic laboratory system, and test demand for types of tests and number of the tests to be performed on samples by the analyzers, wherein the analyzers each include consumable items and maintenance items; and determining, via a walk-away time estimation module executing on the system controller, an estimated walk-away time for the analyzers and a lowest estimated walk-away time for the diagnostic laboratory system based upon the test demand and status of the consumable items and maintenance items.

2. The status visualization method of claim 1, comprising displaying the estimated walk-away time for each of the analyzers.

3. The status visualization method of claim 1, comprising displaying the estimated walk-away time or the lowest estimated walk-away time for the diagnostic laboratory system.

4. The status visualization method of claim 1, wherein the consumable items comprise one or more of:
test-specific reagents,
bulk reagent,
calibrators,
conditioner,
QC liquids,
diluent,
wash liquid,
pipette tips, and
reaction vessels.

5. The status visualization method of claim 1, wherein the maintenance items comprise one or more selected from a group of:
emptying solid waste, and
emptying liquid waste.

6. The status visualization method of claim 1, wherein the types of the tests and the number of the tests to be performed on the samples are provided from a test demand module.

7. The status visualization method of claim 1, comprising providing one or more additional action options selectable to increase the estimated walk-away time for one or more of the analyzers.

8. The method of claim 7, comprising identifying an additional action option of the one or more additional action options that is selectable to increase the estimated walk-away time for one or more of the analyzers.

9. The method of claim 7, further comprising, upon confirming completion of an additional action option of the one or more additional action options, providing a new estimated walk-away time.

10. The method of claim 7, wherein the one or more additional action options comprise, a group of like ones of consumable items or like ones of the maintenance items, for a group of the analyzers.

11. The method of claim 1, comprising receiving in a walk-away items database, additional estimates for replacement of the consumable items and additional estimates for completion of the maintenance items.

12. The method of claim 1, wherein test demand module provides the walk-away time estimation module the test demand based on a historical record of the types of tests and the number of the tests conducted over a previous time period.

13. The method of claim 1, wherein a status of at least some of the consumable items and/or maintenance items are provided by sensing by the analyzers.

14. The method of claim 13, wherein the sensing is based on test counts provided from the analyzers.

15. A status visualization method of a diagnostic laboratory system, comprising:
receiving, at a system controller, non-transitory computer-readable data comprising an inventory of analyzers included within the diagnostic laboratory system, and test demand for types of tests and number of the tests to be performed on samples by the analyzers, wherein the analyzers each include consumable items and maintenance items;

determining, via a walk-away time estimation module executing on the system controller, an estimated walk-away time for the analyzers based upon the test demand and status of the consumable items and maintenance items; and providing one or more additional action options selectable to increase the estimated walk-away time for one or more of the analyzers.

16. The method of claim 15, comprising identifying an additional action option of the one or more additional action options that is selectable to increase the estimated walk-away time for one or more of the analyzers.

17. The method of claim 15, further comprising, upon confirming completion of an additional action option of the one or more additional action options, providing a new estimated walk-away time.

18. The method of claim 15, wherein the one or more additional action options comprise, a group of like ones of consumable items or like ones of the maintenance items, for a group of the analyzers.

19. A status visualization method of a diagnostic laboratory system, comprising:
receiving, at a system controller, non-transitory computer-readable data comprising an inventory of analyzers included within the diagnostic laboratory system, and test demand for types of tests and number of the tests to be performed on samples by the analyzers, wherein the analyzers each include consumable items and maintenance items;

determining, via a walk-away time estimation module executing on the system controller, an estimated walk-away time for the analyzers based upon the test demand and status of the consumable items and maintenance items; and receiving in a walk-away items database, additional estimates for replacement of the consumable items and additional estimates for completion of the maintenance items.

* * * * *